United States Patent
Walker et al.

(10) Patent No.: US 7,777,877 B2
(45) Date of Patent: Aug. 17, 2010

(54) HIGH EFFICIENCY COUPLING OPTICS FOR PUMPING AND DETECTION OF FLUORESCENCE

(75) Inventors: Christopher I. Walker, Pasadena, CA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 338 days.

(21) Appl. No.: 11/876,211

(22) Filed: Oct. 22, 2007

(65) Prior Publication Data

US 2008/0151249 A1    Jun. 26, 2008

Related U.S. Application Data

(60) Provisional application No. 60/853,376, filed on Oct. 20, 2006.

(51) Int. Cl.
*G01N 1/10* (2006.01)
*G01N 21/01* (2006.01)

(52) U.S. Cl. ........................... 356/246; 356/244
(58) Field of Classification Search ......... 356/244–246, 356/455–448
See application file for complete search history.

(56) References Cited

U.S. PATENT DOCUMENTS

| | | | |
|---|---|---|---|
| 3,498,724 A * | 3/1970 | Harrower et al. | 356/246 |
| 4,293,652 A | 10/1981 | Cohen | |
| 4,403,036 A | 9/1983 | Hartley et al. | |
| 4,416,988 A | 11/1983 | Rubin | |
| 4,683,194 A | 7/1987 | Saiki et al. | |
| 4,683,195 A | 7/1987 | Mullis et al. | |
| 4,683,202 A | 7/1987 | Mullis | |
| 5,077,192 A | 12/1991 | Liang et al. | |
| 5,221,610 A | 6/1993 | Montagnier et al. | |
| 5,656,493 A | 8/1997 | Mullis et al. | |
| 5,869,243 A | 2/1999 | Jauregul et al. | |
| 6,814,934 B1 | 11/2004 | Higuchi | |
| 7,282,207 B1 | 10/2007 | Colpitts et al. | |
| 7,282,335 B2 | 10/2007 | Gocke et al. | |
| 7,282,343 B1 | 10/2007 | Abrams et al. | |
| 7,282,350 B2 | 10/2007 | Rao et al. | |
| 7,282,360 B2 | 10/2007 | Meyers et al. | |
| 7,282,366 B2 | 10/2007 | Rambhatla et al. | |
| 7,282,477 B2 | 10/2007 | Schiemann | |
| 7,282,557 B2 | 10/2007 | Zuker et al. | |

(Continued)

OTHER PUBLICATIONS

Saiki et al., Enzymatic Amplification of #-Globin Genomic Sequences and Restriction Site Analysis for Diagnosis of Sickle Cell Anemia, Science; 1985, 230, 4732, pp. 1350-1354.

*Primary Examiner*—Michael P Stafira
(74) *Attorney, Agent, or Firm*—Milstein Zhang & Wu LLC; Joseph B. Milstein

(57) ABSTRACT

The invention provides a high efficiency coupling structure for extracting illumination such as fluorescent radiation from a chemical reaction vessel such as a cuvette. The cuvette is provided with a mirrored surface. An end cap for the cuvette includes a probe portion that exhibits total internal reflection. Lenses are provided in various embodiments that improve the light collection and directing properties of the end cap. A fast optical system for free space coupling of optical radiation emanating from a chemical processing cuvette that uses the end cap as an element is also described.

17 Claims, 16 Drawing Sheets

U.S. PATENT DOCUMENTS 7,282,563 B2 10/2007 Evans et al.
7,282,567 B2 10/2007 Goldenberg et al.
7,282,579 B2 10/2007 Uemura et al.

\* cited by examiner

HIGH EFFICIENCY COUPLING OPTICS FOR PUMPING AND DETECTION OF FLUORESCENCE

CROSS-REFERENCE TO RELATED APPLICATIONS

This application claims priority to and the benefit of U.S. provisional patent application Ser. No. 60/853,376 filed Oct. 20, 2006, which application is incorporated herein by reference in its entirety.

STATEMENT REGARDING FEDERALLY FUNDED RESEARCH OR DEVELOPMENT

The U.S. Government has certain rights in this invention pursuant to Grant No. HR0011-04-1-0032 awarded by DARPA.

FIELD OF THE INVENTION

The invention relates to optical systems in general and particularly to an optical coupler and system that employs total internal reflection to improve the detection of signals of interest.

BACKGROUND OF THE INVENTION

There are numerous instances in scientific and technical endeavors when one desires to observe and measure fluorescent signals. As one example, in the field of biotechnology, it has become common to generate a many-fold increase in a material, such as DNA, RNA or other biologically or medically interesting material, in order to perform tests, obtain diagnoses, do other medically useful procedures, or identify a source of the material for forensic purposes, when only a minute amount of the biologically or medically interesting material is obtained or is available. The amount of material present can be quantified by observing an optical signal, such as a fluorescent signal, from the reaction product itself, or from a substance that chemically combines with the reaction product of interest. By way of example, this is described in many United States patents, including U.S. Pat. Nos. 7,282,579, 7,282,567, 7,282,563, 7,282,557, 7,282,477, 7,282,366, 7,282,360, 7,282,350, 7,282,343, 7,282,335, 7,282,207, 5,869,243, 5,221,610, and 5,077,192, the disclosures of all of which are incorporated herein by reference.

As a broad introduction to these kinds of activities, one can cite the discussion presented by Mullis et al. in U.S. Pat. No. 5,656,493, issued on Aug. 12, 1997, the disclosure of which is incorporated herein by reference. Mullis describes the Polymerase Chain Reaction (PCR) method as an example of a method of increasing the available amount (or "amplifying") material such as DNA.

There are methods for producing nucleic acid sequences in large amounts from small amounts of an existing sequence. Such methods involve cloning of a nucleic acid sequence in an appropriate host system, and culturing the host, wherein the vector in which the nucleic acid sequence has been inserted is replicated, resulting in copies of the vector and hence the Sequence. See T. Maniatis, et al., Molecular Cloning: A Laboratory Manual, Cold Spring Harbor Laboratory, pp. 390-401 (1982); and U.S. Pat. Nos. 4,416,988 and 4,403,036. The original sequence can also be organically synthesized before insertion in a vector. See U.S. Pat. No. 4,293,652.

A method, described by Saiki et al., Science, 230, 1530-1534 (1985), has been devised for amplifying one or more specific nucleic acid sequences or a mixture thereof using primers, nucleotide triphosphates, and an agent for polymerization, such as DNA polymerase. The extension product of one primer, when hybridized to the other, becomes a template for the production of the desired specific nucleic acid sequence, and vice versa. The process is repeated as often as necessary to produce the desired amount of the sequence.

This method is especially useful for performing clinical tests on the DNA or RNA from a fetus or other donor where large amounts of the DNA or RNA are not readily available and more DNA or RNA must be manufactured to have a sufficient amount to perform tests. The presence of diseases which have unique DNA or RNA signatures can be detected by amplifying a nucleic acid sample from a patient and using various probe procedures to assay for the presence of the nucleic acid sequence being detected in the test. Such test might be prenatal diagnosis of sickle cell anemia, as described by Saiki et al., supra, where the amplification of specific B-globin target sequences in genomic DNA resulted in the exponential increase (220,000 times) of target DNA copies, increasing sensitivity and speed while reducing the complexity of diagnosis. Another test is the diagnosis of the AIDS virus, which is thought to alter the nucleic acid sequence of its victims.

Five patent applications which describe the amplification process, PCR, are U.S. patent application Ser. No. 818,127, filed Jan. 10, 1986, now abandoned, U.S. Ser. No. 716,982, filed Mar. 28, 1985, now U.S. Pat. No. 4,683,194, U.S. Ser. No. 791,308, filed Oct. 25, 1985, now U.S. Pat. No. 4,683,202, U.S. Ser. No. 828,144, filed Feb. 7, 1986, now U.S. Pat. No. 4,683,195, and U.S. Ser. No. 839,331, filed Mar. 13, 1986, now abandoned, the disclosures of all of which are incorporated herein by reference.

The amplification method, PCR, bears some similarity to the molecular cloning methods described above, but does not involve propagation of a host organism, avoiding the hazards and inconvenience therein involved. In addition, the amplification method does not require synthesis of nucleic acid sequences unrelated to the desired sequence, and thereby obviates the need for extensive purification of the product from a complicated biological mixture. Finally, the amplification is more efficient than the alternative methods for producing large amounts of nucleic acid sequences from a target sequence and for producing such sequences in a comparatively short period of time.

At first, the amplification procedure, PCR, described above was carried out by hand in the laboratories. The manual process involves a great deal of repetitive liquid handling steps and incubations at controlled temperatures. This is not only time-consuming and tedious, but it is also subject to error caused by human operator attention span drift. Such errors could result in a misdiagnosis of a genetic birth defect and an unnecessary abortion or the lack of an abortion where a birth defect exists. Further, such errors could result in misdiagnosis of sickle cell anemia or other genetic disorders.

Further, certain nucleic acids amplify more efficiently than others, so some nucleic acid sequence amplifications require more amplification cycles than others because the cost of laboratory labor can be high, and the risks to which a laboratory is subjected are high in case of error in erroneously performing amplification, there has arisen a need for a system which can automate the amplification process.

Mullis then described a system for use in performing an automated amplification process.

The amplification process, PCR, maybe conducted continuously. In one embodiment of an automated process, the reaction may be cycled through a denaturing region, a reagent addition region, and a reaction region. In another embodiment, the enzyme used for the synthesis of primer extension products can be immobilized in a column. The other reaction components can be continuously circulated by a pump through the column and a heating coil in series; thus the nucleic acids produced can be repeatedly denatured without inactivating the enzyme.

One embodiment of a machine for automating the amplification process utilizes a liquid handling system under computer control to make liquid transfers of enzyme stored at a controlled temperature in a first receptacle into a second receptacle whose temperature is controlled by the computer to conform to a certain incubation profile. The second receptacle stores the nucleic acid sequence to be amplified plus certain reagents. The computer includes a user interface through which a user can enter process parameters which control the characteristics of the various steps in the sequence such as the times and temperatures of incubation, the amount of enzyme to transfer on each cycle into the second receptacle from the first receptacle, as well as the number of cycles through the amplification sequence that the user desires the machine to perform. The first and second receptacles may be controlled in temperature by use of three circulating fluid reservoirs and solenoid operated valves. Of course, any other method for controlling the temperatures of the receptacles will also work for purposes of the invention, and the invention is not limited to the use of heated and chilled circulating fluids. These solenoid operated valves are coupled to the computer such that the proper temperature fluid can be directed through the supporting structure for the first and second receptacles at the proper times in the PCR sequence under computer control. The first receptacle, which stores enzyme to be added to the reaction well of the second receptacle, is kept at a constant temperature. The second receptacle, which is where the PCR reaction occurs, is switched under computer control between two temperatures by the transmission of a control signal to the solenoid operated valves at the proper time in the sequence to gate either the hot fluid or the cold fluid through the support structure of the second receptacle.

While the above-described machine increases the amount of nucleic acid sequence which can be amplified per unit of labor, thereby decreasing the possibility of error, it involves liquid handling, where reagents must be continuously transferred at various cycles. There is a need also for a machine which not only automates the amplification process, but also makes it faster and more convenient. This can be accomplished using an enzyme which is thermostable, i.e., will not break down when subjected to denaturing temperatures.

A second embodiment of the invention utilizes a temperature-cycling instrument for implementing the amplification process when a thermostable enzyme is employed. The use of a thermostable enzyme avoids the need for liquid transferring of the enzyme, which is necessitated when the enzyme is unstable in the presence of heat. As used herein to describe enzymes, "thermostable" means stable at temperatures above 90 degree C. and "heat-stable" means stable at temperatures 65 degree-90 degree C.

In U.S. Pat. No. 6,814,934, issued Nov. 9, 2004, which is incorporated herein by reference, Higuchi describes methods of monitoring the amplification of nucleic acids. The sensitivity and specificity of nucleic acid detection methods was greatly improved by the invention of the polymerase chain reaction (PCR). PCR is a process for amplifying nucleic acids and involves the use of two oligonucleotide primers, an agent for polymerization, a target nucleic acid template, and successive cycles of denaturation of nucleic acid and annealing and extension of the primers to produce a large number of copies of a particular nucleic acid segment. With this method, segments of single copy genomic DNA can be amplified more than 10 million fold with very high specificity and fidelity. PCR methods are disclosed in U.S. Pat. No. 4,683,202, which is incorporated herein by reference. PCR and other methods of amplifying biologically or medically interesting material are well known and will not be further discussed herein.

There is a need for an improved apparatus and method for collecting optical signals such as fluorescent signals, so that one can obtain results in shorter times, using less material, and from less concentrated reaction media.

SUMMARY OF THE INVENTION

In one aspect, the invention relates to an end cap for a chemical processing cuvette with integrated optical analytical capability. The end cap comprises a sealing portion of the end cap for sealing the cuvette, the sealing portion configured to provide a liquid-tight seal to the cuvette; and an optical probe portion of the end cap, the optical probe portion configured to provide optical confinement of light therein, the optical probe portion configured to avoid physical immersion in a fluid contained within the cuvette.

In one embodiment, the optical probe portion comprises a lens at the distal end thereof. In one embodiment, the optical probe portion comprises a structure configured to provide total internal reflection. In one embodiment, the end cap further comprises a shoulder section configured to center the probe section within the cuvette. In one embodiment, the end cap further comprises a lens disposed on an end of the end cap external to the cuvette.

In another aspect, the invention features a fast optical system for free space coupling of optical radiation emanating from a chemical processing cuvette. The fast optical system comprises an illumination source configured to provide pump radiation at a first wavelength; a detector configured to receive a beam of electromagnetic radiation at a wavelength different from the pump radiation at the first wavelength, and configured to provide an output signal representing at least one property of the received electromagnetic radiation; a computer-based controller for controlling the illumination source and the detector, and additionally configured to analyze the output signal provided by the detector and to provide a result based on the output signal; a chemical processing cuvette configured to contain a liquid of interest; an end cap for a chemical processing cuvette with integrated optical analytical capability as described hereinabove; a beam splitter and filter configured to pass pump radiation at the first wavelength into the chemical processing cuvette by way of the end cap, and configured to pass electromagnetic radiation at a wavelength different from the pump radiation at the first wavelength from the cuvette by way of end cap to the detector; and one or more lenses separated from the end cap, the one or more lenses configured to shape the beam of electromagnetic radiation to illuminates the detector.

In one embodiment, the end cap for a chemical processing cuvette comprises a lens at the distal end thereof. In one embodiment, the optical probe portion comprises a structure configured to provide total internal reflection. In one embodiment, the fast optical system further comprises a shoulder section configured to center the probe section within the cuvette. In one embodiment, the fast optical system further comprises a lens disposed on an end of the end cap external to the cuvette. In one embodiment, the one or more lenses separated from the end cap comprise a concave-spherical, convex elliptical asphere. In one embodiment, the beam splitter is a dichroic filter. In one embodiment, the beam splitter comprises a partially transparent mirror and a filter. In one embodiment, the source of pump illumination is a laser. In one embodiment, the source of pump illumination is a light emitting diode. In one embodiment, the source of pump illumination is a source of illumination configured to provide a broad range of wavelengths and an associated monochromator.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

It is well known to collect and detect optical signals such as fluorescence from the side of a capillary-style cuvette containing a reaction medium. Essentially, in standard liquid fluorescence measurements, the amount of light collected is limited by the solid angle described by a detector spaced at some distance away from the sample.

Figure 1:
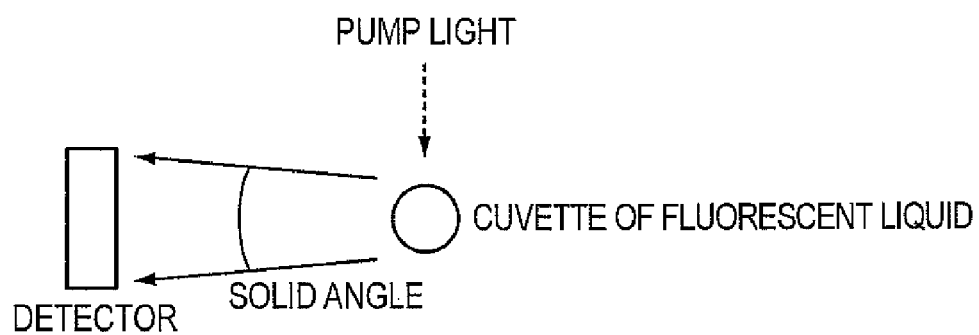
FIG. 1 illustrates a prior art method of collecting a fluorescent signal from a conventional cuvette.

FIG. 1 illustrates a prior art method of collecting a fluorescent signal from a conventional cuvette. For example, a circular detector with radius r placed a distance d away from a cuvette which is small in both dimensions with respect to the detector, would collect light with an efficiency given approximately by Eqn. 1.

$$e = \frac{1}{2}\left(1 - \frac{1}{\sqrt{1 + \left(\frac{r}{d}\right)^2}}\right) \quad \text{Eqn. 1}$$

For a detector of radius 10 mm, spaced 20 mm away from a small cuvette, this results in an expected collection efficiency of about 1.4%.

Another approach that can be employed involves detection of illumination along the long axis of the capillary-style cuvette. Detection of fluorescence (or other optical signal) in capillaries from the top down presents unique challenges. In general, a cap is placed over the capillary-style cuvette during the processing of the material within the capillary-style cuvette. Light exiting the capillary-style cuvette is coupled from the fluid to the sealing cap, from the cap into free space, and from the free space mode into the detector. The light from a light source traverses a similar path in the opposite direction. In one embodiment, the capillary-style cuvette is quartz, and the cap is a plastic which is optically clear at the pump and fluorescence wavelengths. Other materials that are suitably chemically and thermally inert, and that have acceptable optical characteristics could be used as alternative media of construction for the capillary-style cuvette and/or the cap.

Figure 2:
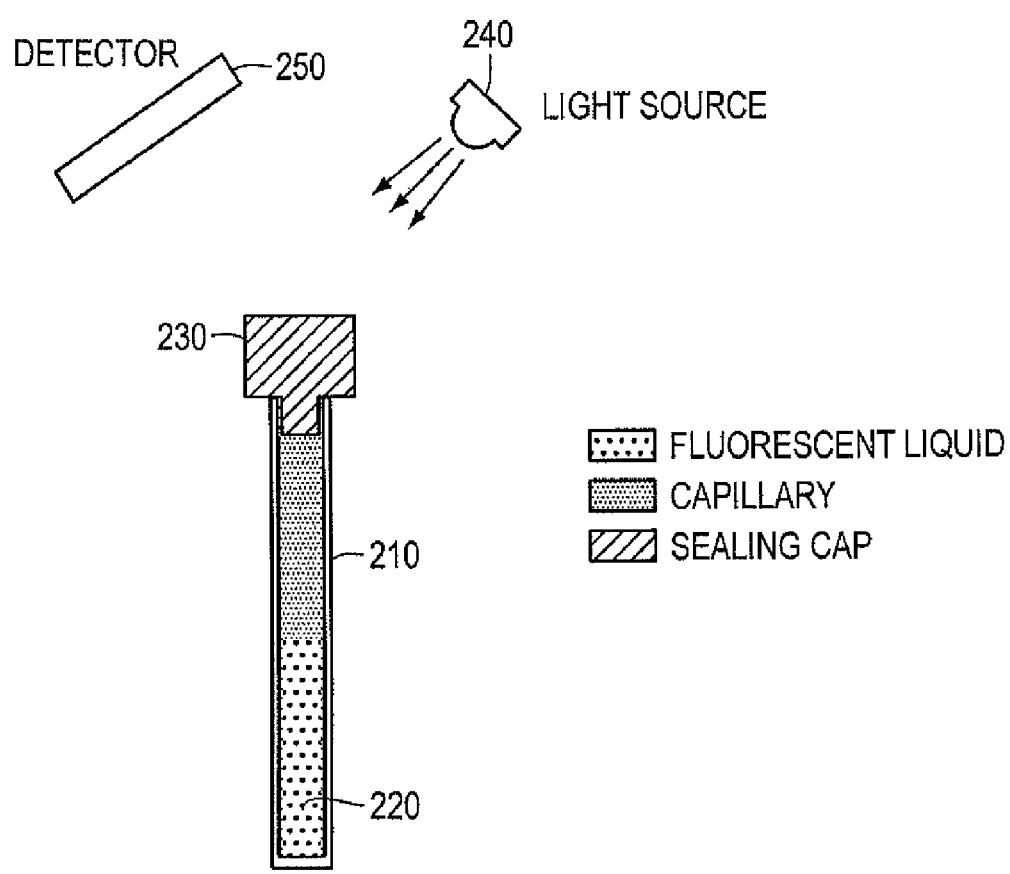
FIG. 2 is a diagram that schematically illustrates the relationships among the capillary-style cuvette that holds the fluorescent liquid, the sealing cap, the pump light source, and the detector, according to principles of the invention.

FIG. 2 is a diagram that schematically illustrates the relationships among the capillary-style cuvette 210 that holds the fluorescent liquid 220, the sealing cap 230, the pump light source 240, and the detector 250.

In some embodiments, a surface of the capillary-style cuvette can be treated to reflect illumination at least in a range of wavelengths of interest. The surface that is treated can in principle be either or both of the inside surface and the outside surface of the capillary-style cuvette. In most instances, it is more convenient (and less likely to introduce unwanted chemical interactions) if the outside surface of the capillary-style cuvette is treated (or is constructed) to be reflective in at least a range of wavelengths of interest, such as the wavelength of the fluorescent radiation, and/or he wavelength of the pump illumination.

In geometries where the outside of the capillary-style cuvette is at least partially mirrored the capillary-style cuvette will act as a light guide in the mirrored section. Light from the fluorescence will be sufficiently randomized from multiple reflections within the mirrored capillary-style cuvette that it will exit the mirrored portion with a quite uniform spatial distribution, and a nearly uniform angular distribution.

By coating the outside of the cuvette with a reflective substance, the light is collected over the entire solid angle of $4\pi$ steradians, and is only allowed to exit through the top of the cuvette. The exterior may be made reflective by a number of means, including coating with a thin layer of a reflective metal, such as aluminum or gold, immersion in a liquid metal, such as gallium or mercury, or coated with a dichroic thin film stack for single wavelength containment. The light will be contained up to the end of the reflective layer, as shown in FIG. 3.

Figure 3:
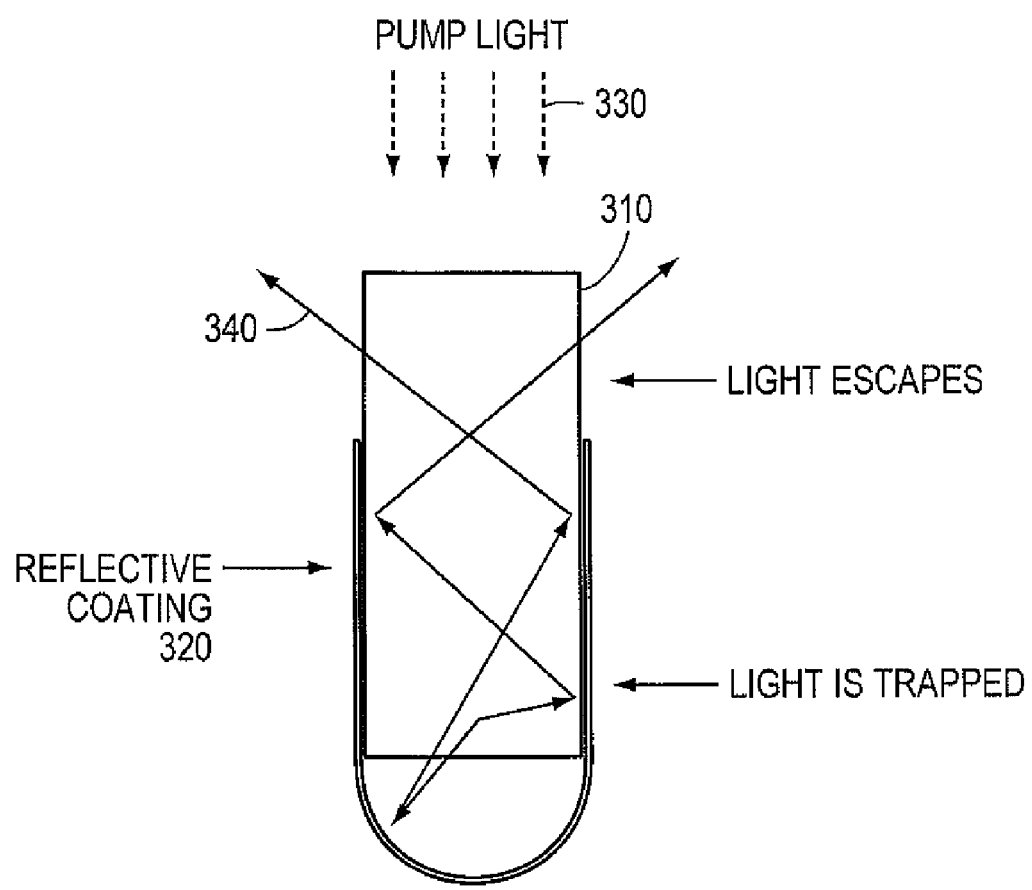
FIG. 3 is a diagram illustrating the behavior of illumination in the cuvette, according to principles of the invention.

FIG. 3 is a diagram illustrating the behavior of illumination in the cuvette 310. As may be seen in FIG. 3, a reflective coating 320 is applied to the cuvette, for example on its exterior surface. Pump light 330 is allowed to enter the open end of the cuvette 310, as illustrated by the dotted arrows. Light present within the cuvette, whether pump light or fluorescent light, is effectively trapped by the mirrored section at the closed end of the cuvette, and can escape at the open end of the cuvette, as illustrated by arrows 340.

As is now described, the improvement provided by the present invention relates to how the device (guiding cuvette) works by collecting light from the entire angular space, and focusing it into a cap comprising a light guide, and one or more focusing lenses, including one or more lenses separated from the cap.

Optical Coupling Between the Liquid and the Cap

According to the present invention, there is provided a cap for the cuvette or capillary-style cuvette. The cap comprises an optical probe portion which extends into the capillary-style cuvette to couple the light into the cap structure. The end of the probe nearest the liquid in the capillary-style cuvette may be lensed. In some embodiments, the optical probe portion comprises a structure configured to provide total internal reflection.

Figure 4:
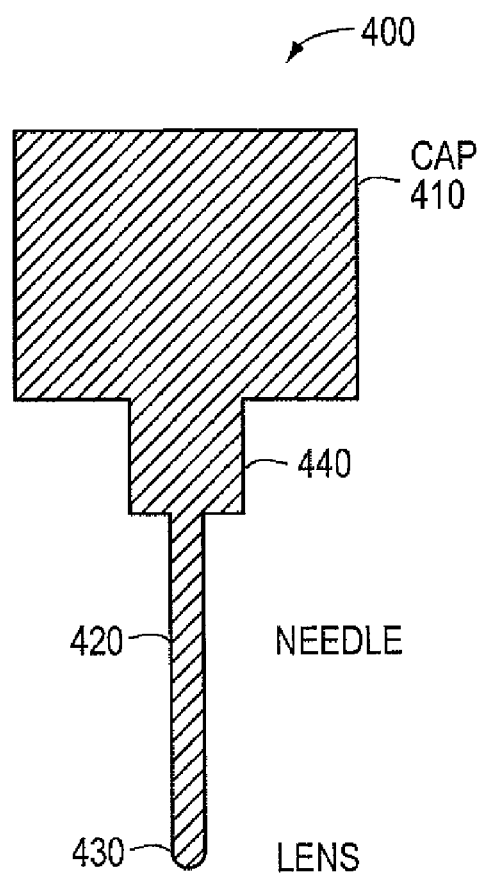
FIG. 4 is a cross-sectional illustration of a first design of a cap comprising a probe, according to principles of the invention.

FIG. 4 is a cross-sectional illustration of a first design of a cap 400 comprising a probe. In FIG. 4, the cap 400 has a portion 410 that remains external to the cuvette. A probe in the form of a needle 420 that is thin enough to fit within the inside diameter of the cuvette (assuming a round cuvette) is provided. The needle 420 can be constructed with a lens 430 at its distal end (e.g., at the end closest to the material held within the cuvette, and farthest from the open end of the cuvette). For convenience, a shoulder section 440 can be provided to center the needle within the cuvette. In some embodiments, the needle 420 is designed to be nearly as large in diameter as the shoulder 440, so as to substantially fill the entire internal dimension of the cuvette. For ease of construction, and in order to keep the costs of manufacture as low as possible, there in general will be some tolerance between the inside diameter of the cuvette and the outside diameter of the needle 410.

Figure 5:
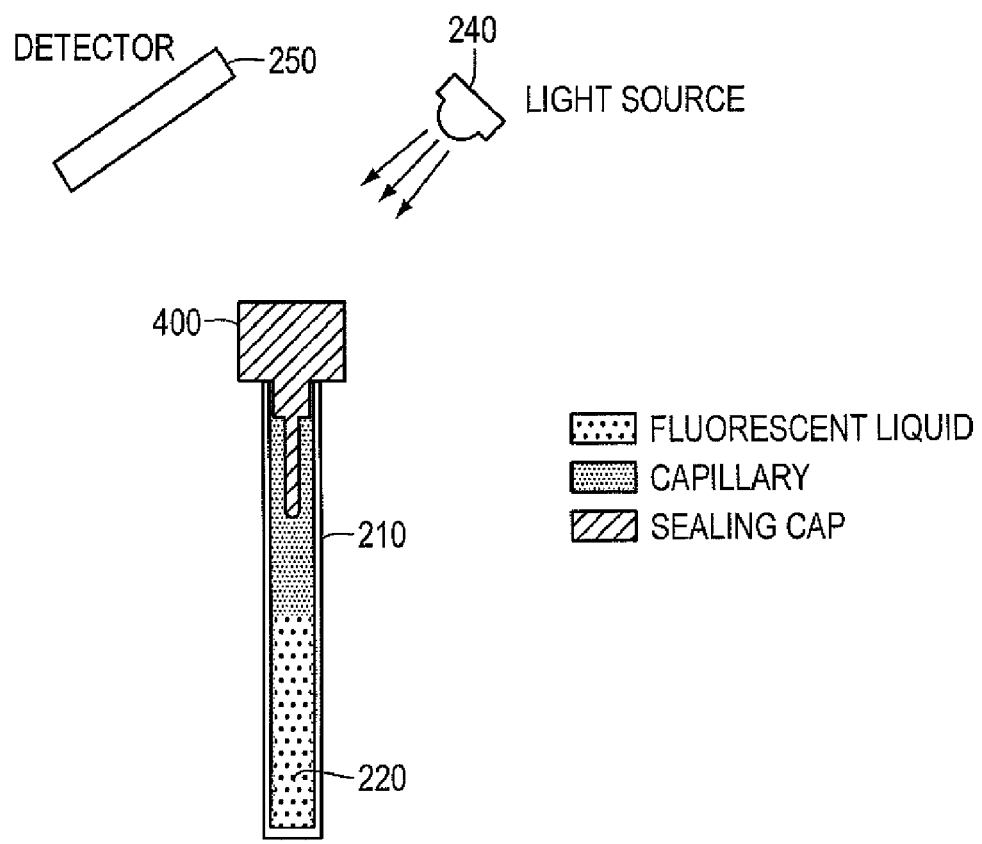
FIG. 5 is a diagram similar to FIG. 2, that schematically illustrates the cap of FIG. 4 in relation to the cuvette, the liquid, the pump light and the detector, according to principles of the invention.

FIG. 5 is a diagram similar to FIG. 2, that schematically illustrates the cap 400 of FIG. 4 in relation to the cuvette 210, the liquid 220, the pump light 240 and the detector 250.

The probe 420 captures light from the free space, scattered modes inside the capillary-style cuvette, and acts as a light pipe to carry the light to the surface of the cap. No contact with the liquid is necessary. Even a short (a few capillary diameters) extension of the probe into the capillary-style cuvette will suffice. Coupling efficiency is determined primarily by the diameter of the probe. The greater the radial area filled by the probe, the higher the efficiency.

Figure 6:
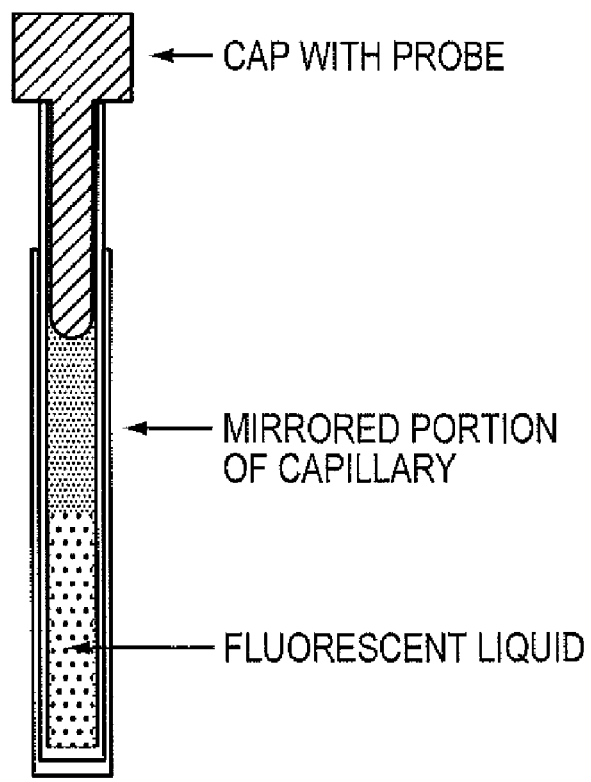
FIG. 6 is a schematic diagram that illustrates the mechanical and optical relationships of the cap comprising the probe when it is assembled with a capillary-style cuvette having a mirrored portion and containing a liquid, according to principles of the invention.

FIG. 6 is a schematic diagram that illustrates the mechanical and optical relationships of the cap 400 comprising the probe 420 when it is assembled with a capillary-style cuvette 310 having a mirrored portion 320 and containing a liquid 220.

By channeling the light contained in the reflective cuvette into a lightguide, the light can be efficiently extracted. Such a guiding cuvette will have substantially better signal extraction than a conventional system. A cap made of transparent material, which seals to the cuvette and has a probe element which extends past the edge of the reflective layer, though not necessarily into the liquid, will collect the trapped light as shown in FIG. 7.

Figure 7:
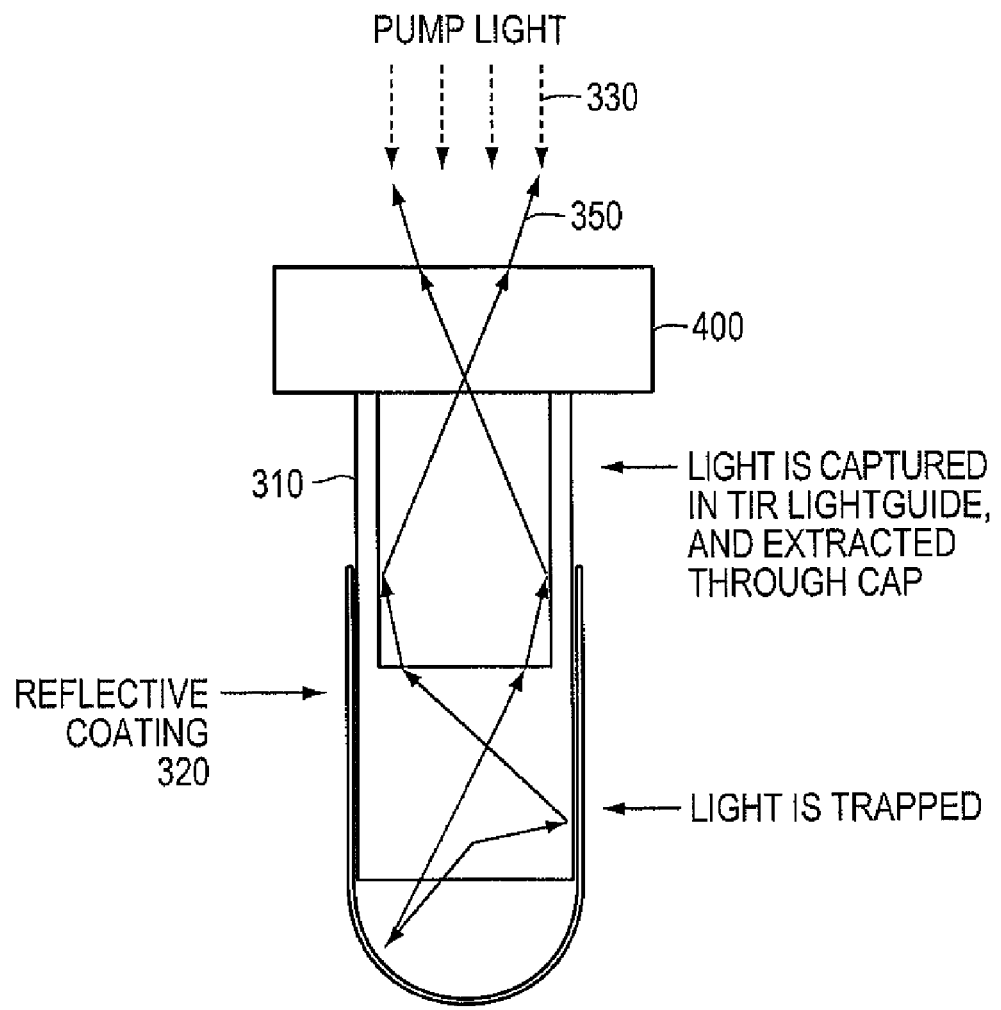
FIG. 7 is a diagram illustrating the behavior of illumination in the cuvette 310 with the addition of a cap, according to principles of the invention.

FIG. 7 is a diagram illustrating the behavior of illumination in the cuvette 310 with the addition of a cap 400. As may be seen in FIG. 7, a reflective coating 320 is applied to the cuvette 310, for example on its exterior surface. Pump light 330 is allowed to enter the open end of the cuvette 310 by way of the cap 400, as illustrated by the dotted arrows. Light present within the cuvette, whether pump light or fluorescent light, is effectively trapped by the mirrored section at the closed end of the cuvette. Exiting light 350 leaves the cuvette at its open end by way of the cap 400.

Optical Coupling from the Cap to Free Space

Figure 8:
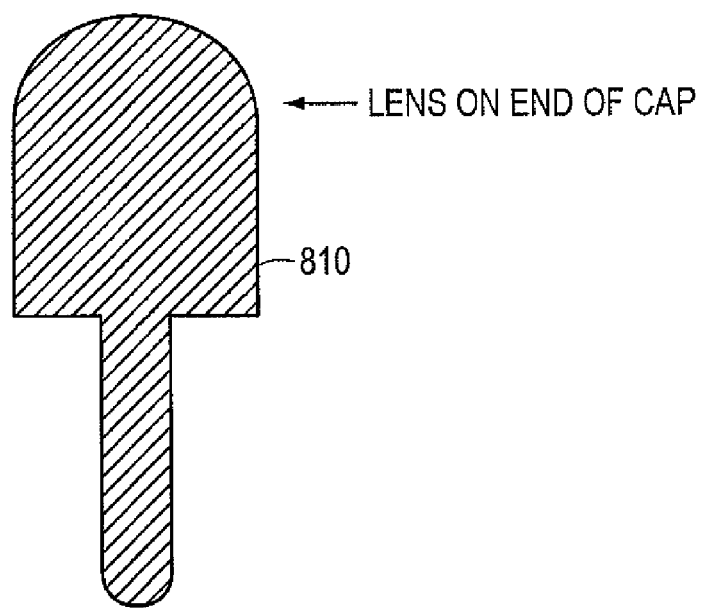
FIG. 8 is a cross sectional diagram of a cap comprising a lens on the end external to the cuvette, according to principles of the invention.

If the cap 400 has a flat top, the fluoresced light is highly divergent at the exit of the cap. A very fast optical system is needed to efficiently collect the fluoresced light. In one embodiment, a cap 810 having a lens incorporated into the structure of the cap 810 external to the cuvette is shown in FIG. 8. In one embodiment, a simple ball lens can be used to greatly increase the convergence of the exiting light. In other embodiments; aspherical lens shapes may be used as well to reduce aberration.

Fast Optical System for Collimation

Figure 9:
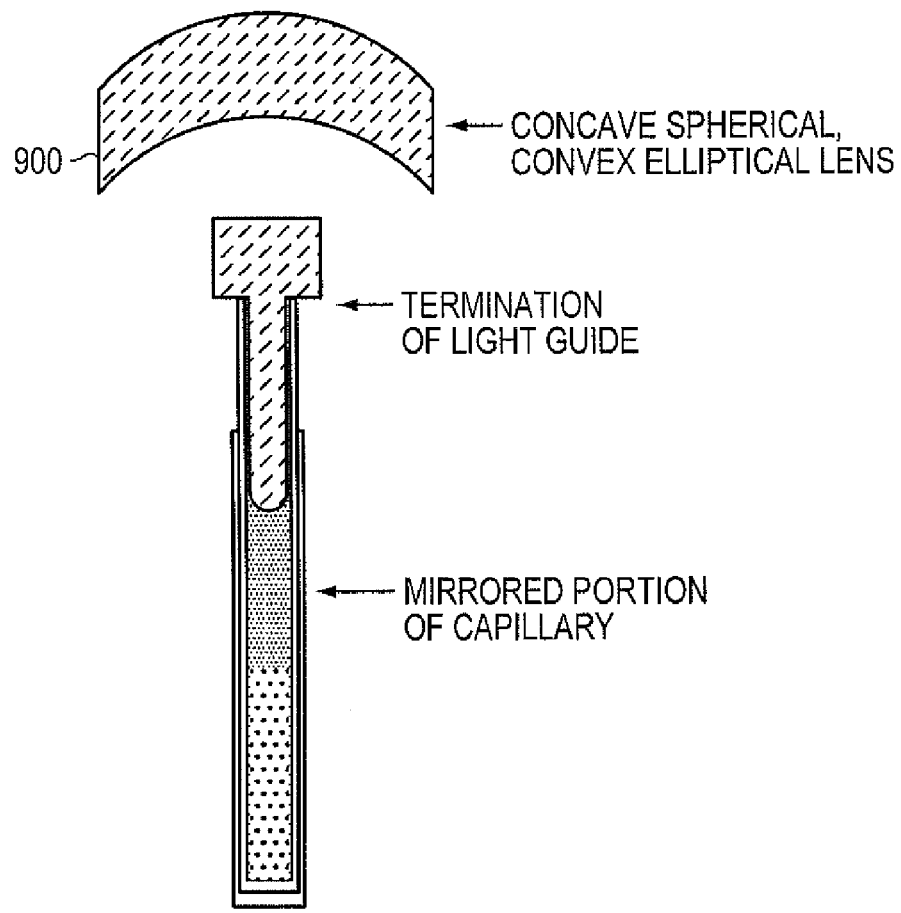
FIG. 9 is a cross sectional diagram of a cap comprising a flat external top and a concave-spherical, convex elliptical asphere lens, according to principles of the invention.

In other embodiments, a lens on the cap is not used. A fast optical system to couple the highly divergent output of the cap to a collimated beam is advantageous. A compact single element solution is the use of a concave-spherical, convex elliptical asphere 900, as illustrated in FIG. 9, where the cap has a flat external top surface. Such designs are well understood, and produce an aberration-free collimated beam. When used in a system of this type, such a lens allows for a much smaller set of coupling optics, and thus overall reduced system size. The lens is positioned such that the nominal center point of the concave sphere is optically coincident with the virtual source at the termination of the probe within the cap as shown in FIG. 9.

System Schematics

Lensed Non-Contact Probe

Figure 10:
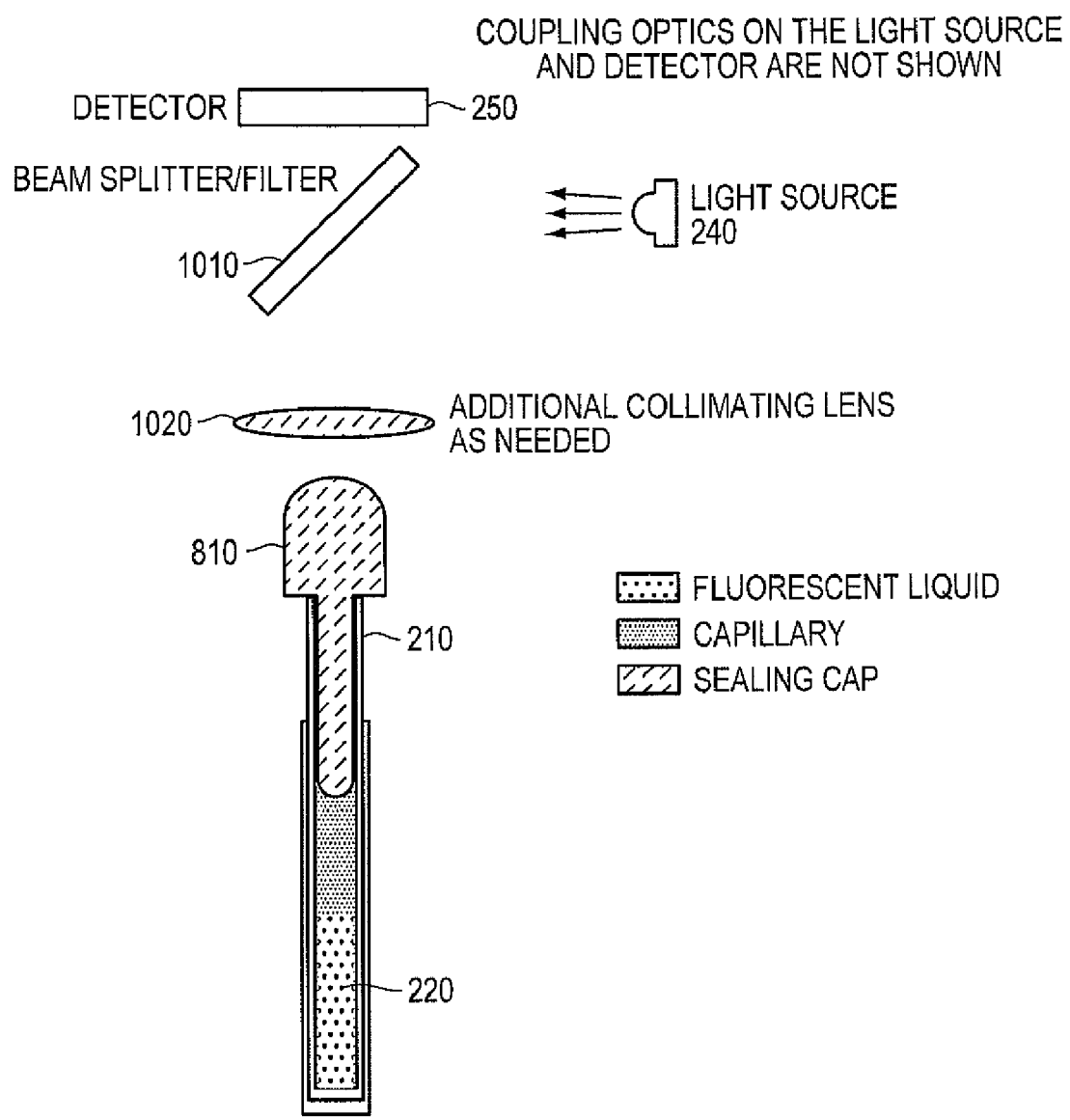
FIG. 10 is a schematic diagram of a first illustrative embodiment of a system comprising a cuvette, a cap having a lens external to the cuvette, a light source, a detector, a beam splitter/filter and one or more additional collimating or beam shaping lenses, according to principles of the invention.

FIG. 10 is a schematic diagram of a first illustrative embodiment of a system comprising a cuvette 210, a cap 810 having a lens external to the cuvette 210, a light source 240, a detector 250, a beam splitter/filter 1010 and one or more additional collimating or beam shaping lenses 1020 as may be required. A liquid comprising a fluorescing material 220 is present in the cuvette 210. As is known in the art, the beam splitter/filter 1010 allows pump radiation having a first wavelength to enter the cuvette 210 by way of the cap 400, and allows fluorescent radiation having a second wavelength to pass through to the detector 250.

Unlensed Non-Contact Probe with Aspheric Collimating Lens.

Figure 11:
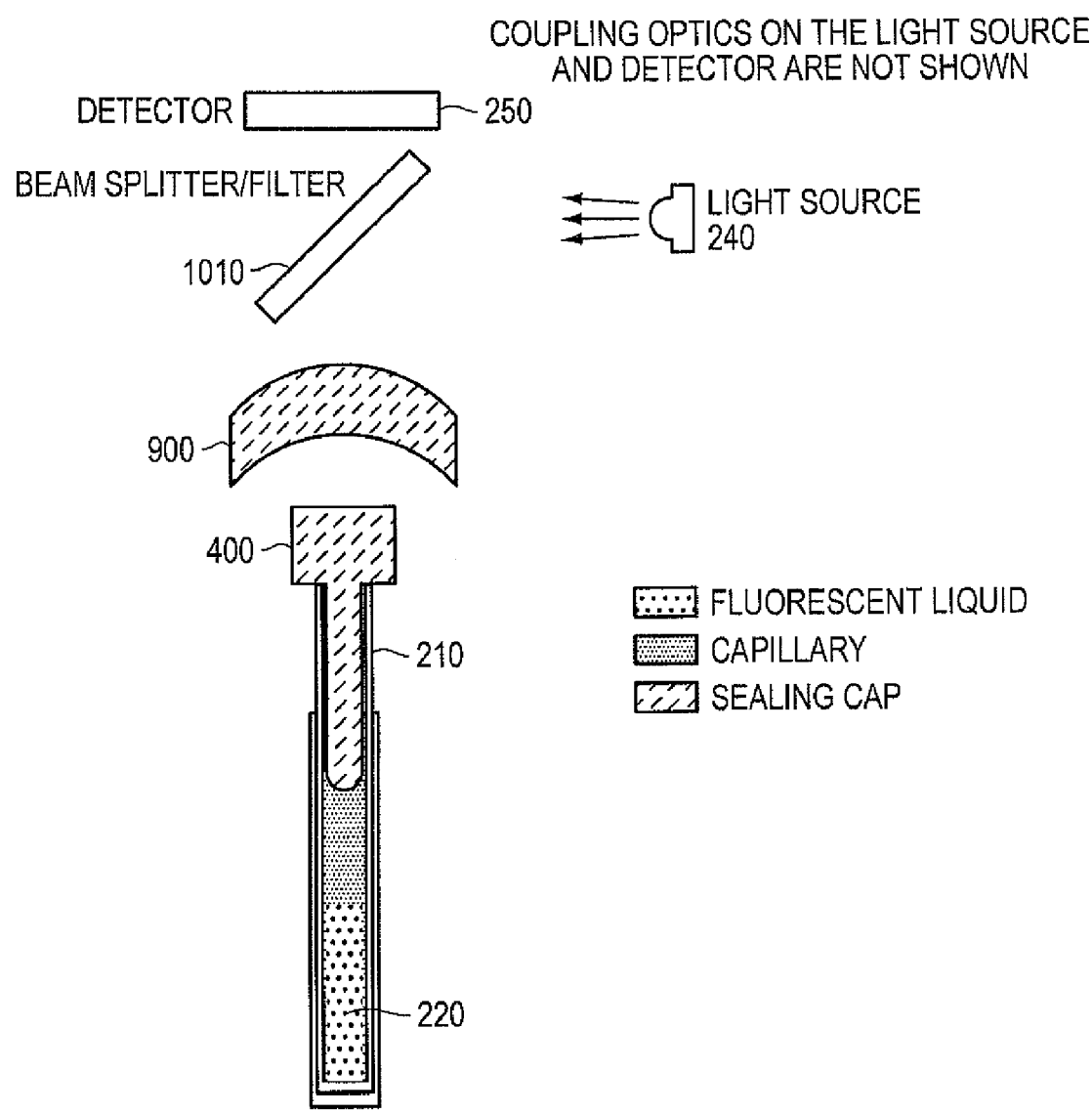
FIG. 11 is a schematic diagram of a first illustrative embodiment of a system comprising a cuvette, a cap having a flat top external to the cuvette, a light source, a detector, a beam splitter/filter and a concave-spherical, convex elliptical asphere, according to principles of the invention.

FIG. 11 is a schematic diagram of a first illustrative embodiment of a system comprising a cuvette 210, a cap 410 having a flat top external to the cuvette 210, a light source 240, a detector 250, a beam splitter/filter 1010 and a concave-spherical, convex elliptical asphere 900, as illustrated in FIG. 9. A liquid comprising a fluorescing material 220 is present in the cuvette 210. As is known in the art, the beam splitter/filter 1010 allows pump radiation having a first wavelength to enter the cuvette 210 by way of the cap 400, and allows fluorescent radiation having a second wavelength to pass through to the detector 250.

For either system, one expects to use a general purpose programmable computer operating under the control of instructions provided as software as a controller for operating the source of illumination, as a controller for the detector and as an analyzer for the optical signals received at the detector. The general purpose computer is configured to provide a result based on said output signal, which result can be stored, displayed, printed or otherwise made known to a user, or saved for later use. The general purpose programmable computer can be any convenient computer as described in greater detail here in below. Software to operate the computer to control the illumination source and the detector and to analyze the received optical signals is straightforward, and there are known systems that presently accomplish such control and analysis tasks.

Light Collection

Figure 12:
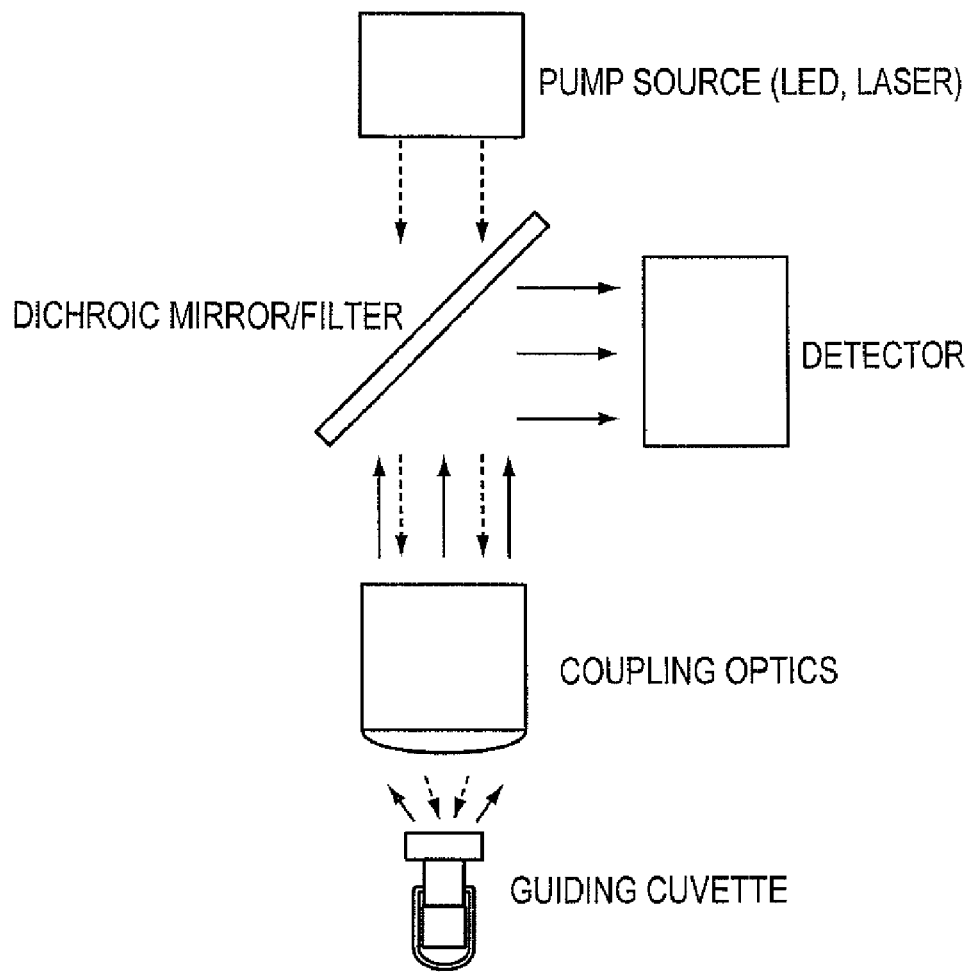
FIG. 12 is a diagram illustrating one embodiment of the filter/source/detector system used in conjunction with the guiding cuvette, according to principles of the invention.

From raytraced models, the light coming out of the end of such a cap has a nearly Gaussian angular distribution, with a fairly wide angular spread. Thus, a lens system with a high numerical aperture (NA) can capture the light fairly efficiently, and collimate it to a filter-detector-source block. Such systems include off the shelf molded aspheres, such as those available from Newport and LightPath, multi-element achromat systems, from a variety of vendors, and long working distance microscope objectives, such as those produced by Mitutoyo. A suitable filter/source/detector system is one such as is used in commercially available products, such as the Roche LightCycler. Furthermore, the cap itself may have a simple lens molded on the outside face to improve collimation. FIG. 12 is a diagram illustrating one embodiment of the filter/source/detector system used in conjunction with the guiding cuvette. As indicated in FIG. 12, the pump source of illumination can in various embodiments be a laser, a light emitting diode, or some other source of illumination at a wavelength of interest, including a source of illumination configured to provide a broad range of wavelengths and an associated monochromator.

Modeling Results of an Optical System

Figure 13:
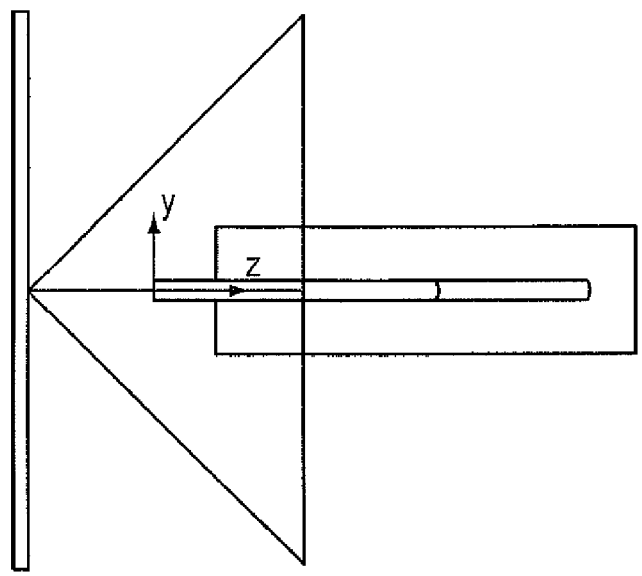
FIG. 13 is a cross sectional diagram of a modeled system that shows the capillary-style cuvette, with a transparent liquid (water), encased in a reflecting solid.

A system based on the capillary-style cuvette used in the Roche LightCycler was modeled using stochastic raytracing techniques. The models were based on the capillary-style cuvette used in the Roche LightCycler, which is a long, thin quartz cuvette. FIG. 13 is a cross sectional diagram of a modeled system that shows the capillary-style cuvette, with a transparent liquid (water), encased in a reflecting solid. A random light source, representing fluorescence was placed in the tip of the capillary-style cuvette, and all light exiting the capillary-style cuvette was assumed to be collected on an infinite area disk. Nominally, all of the light should be collected. However, the model indicated that only 83% of the light would be collected.

Figure 14:
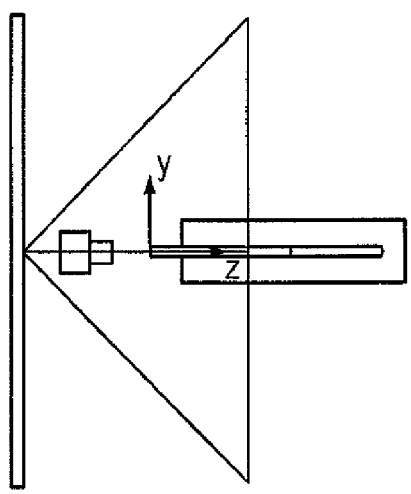
FIG. 14 is a cross sectional diagram of a modeled system that shows the capillary-style cuvette system of FIG. 13 with a transparent cap, according to principles of the invention.

FIG. 14 is a cross sectional diagram of a modeled system that shows the capillary-style cuvette with a transparent cap, with the same nominal dimensions as the actual cap in the Roche capillary-style cuvette, that was placed at the nominal exit of the capillary-style cuvette, and a shielding plane was added, which prevented any light not exiting through the cap from being collected. Approximately 1% of the total light (1.2%, when normalized to the model) was collected.

Figure 15:
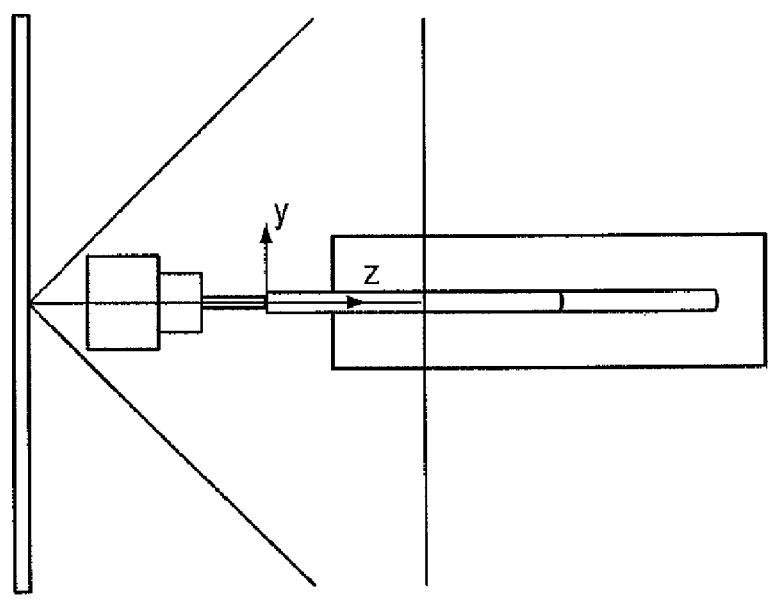
FIG. 15 is a cross sectional diagram of a modeled system that shows the capillary-style cuvette with a transparent cap to which a lightguide was added, according to principles of the invention.

FIG. 15 is a cross sectional diagram of a modeled system that shows the capillary-style cuvette with a transparent cap to which a lightguide was added. The lightguide extended past the boundary of the reflector, but not into the liquid. This allowed rays from within the capillary-style cuvette to be efficiently collected and transferred through the cap. In this system, 13.9% (16.7% corrected to the model) of the light was extracted. Furthermore, the angular distribution of the exiting light is fairly Gaussian one (though very spread out).

Exiting Irradiance Versus Position on the Receiver

Figure 16:
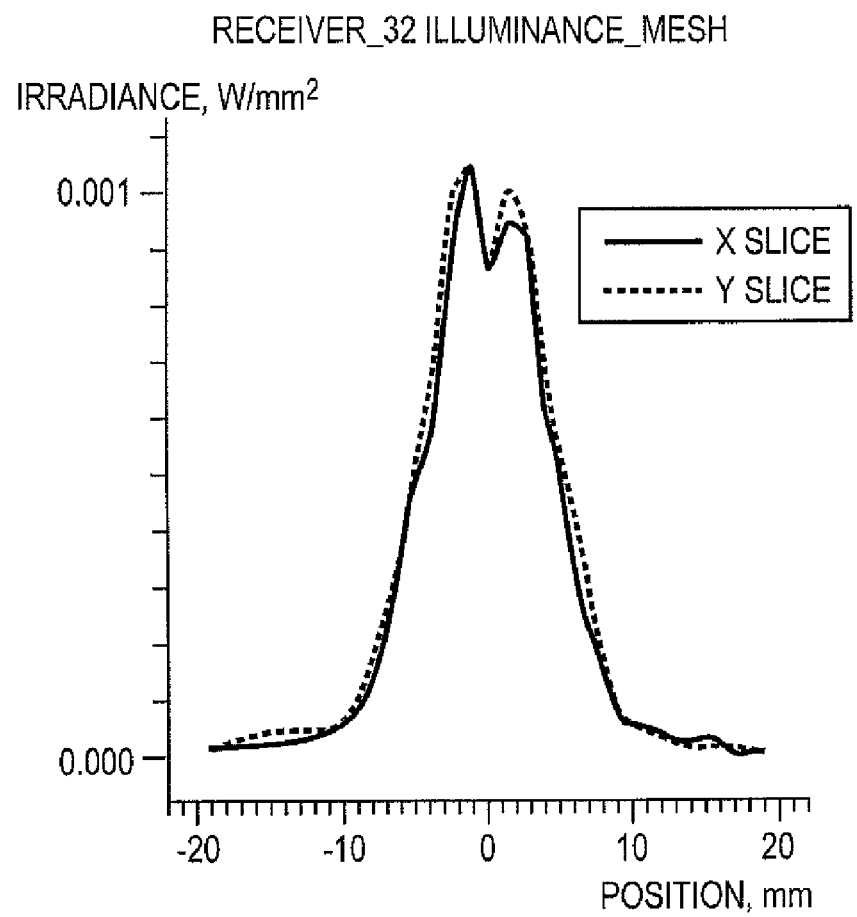
FIG. 16 is a diagram showing the variation in illumination at the receiver, according to principles of the invention.

The receiver is assumed to be spaced approximately 10 mm back from the back face of the cap. FIG. 16 is a diagram showing the expected variation in illumination at the receiver. The vertical axis has units of watts/millimeter$^2$. The horizontal axis represents position in millimeters relative to the center of the receiver. Plots for slices in two orthogonal directions are shown.

Figure 17:
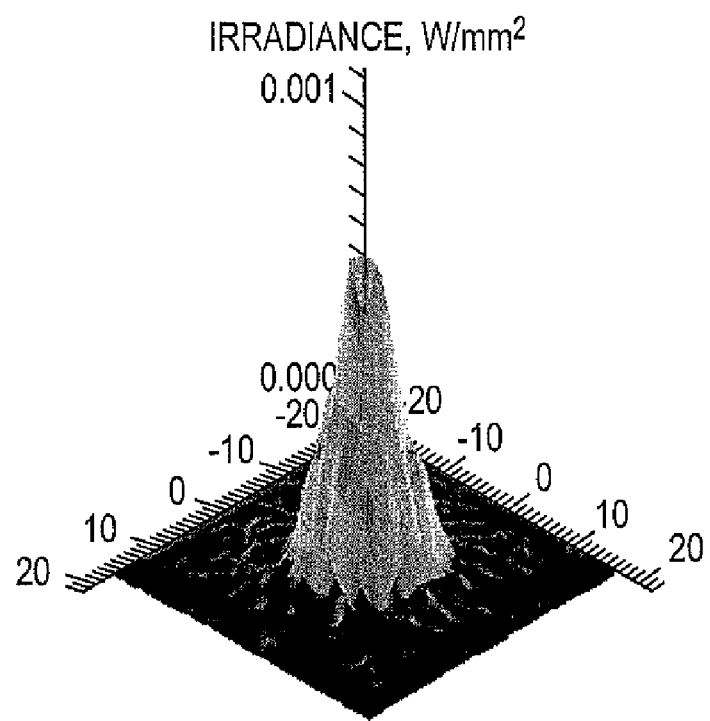
FIG. 17 is a three dimensional diagram showing the irradiance observed at the receiver (in units of watts/millimeter$^2$).

FIG. 17 is a three dimensional diagram showing the irradiance expected to be observed at the receiver (in units of watts/millimeter$^2$).

These results are for converting a commercially available system, which is not optimized for this design, and thus can be substantially improved for a cuvette and illumination system designed as a guided cuvette. Even so, the expected collection efficiency is large (nearly 17%), which is much higher than the expected efficiency of a traditional liquid fluorescence system.

Applications

As the above modeling work demonstrates, the guided cuvette could be used in a Roche LightCycler, for real-time PCR. For real time PCR applications where the goal is to produce a sample of a specific DNA concentration, the guided cuvette would allow for a reduced optical pump power. For real time PCR applications where the goal is simply detection of the presence of a sample, the guided cuvette allows for a reduced number of PCR cycles, leading to a faster test. A more sensitive test would also allow detection of signals from smaller quantities of material.

In general, by increasing the collection efficiency in any liquid fluorescence measurement system, the amount of pump power may be reduced, which reduces bleaching/damage effects on the sample, or the sensitivity of the detection may be improved, leading to faster, more accurate tests.

One simple example is the fluorescence detection of a chemical in solution with an integrating detector. By increasing the detection efficiency by a factor of 10, concentration levels of that chemical can be determined 3 times more accurately, without increasing the optical source power or integration time, or measured to the same accuracy in about $\frac{1}{3}$ of the time. By boosting the collection efficiency by a factor of 50 (from 1% collection to 50% collection), we can obtain results about 7 times more accurately, or in $\frac{1}{7}$ of the time.

General Purpose Programmable Computers

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of Unix, or of Linux.

In operation, a general purpose programmable computer is programmed with instructions in the form of software or firmware. The instructions control the operation of the general purpose programmable computer/The general purpose programmable computer can perform a variety of manipulations of data, such as mathematical operations (e.g., calculations), logical operations (e.g., comparisons, or logical deductions following defined rules), and processing of textual or graphical data (e.g., word processing, or image processing). Data can be provided to the general purpose programmable computer as recorded data or as real-time data. The result of any computation or processing operation is recorded in a machine-readable medium or memory for immediate use or for future use. For example, in micro-processor based analysis modules, data can be recorded in a register in a microprocessor, in a cache memory in the microprocessor, in local memory such as semiconductor memory (e.g., SRAM, DRAM, ROM, EPROM), magnetic memory (e.g., floppy disc or hard disc) and/or optical memory (e.g., CD-ROM, DVD, HD-DVD), or in a remote memory such as a central database. Future use of data recorded in a machine-readable medium can include displaying, printing, or otherwise communicating the data to a user, using the data in a further calculation or manipulation, or communicating the data to another computer or computer-based device.

Machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

While the present invention has been particularly shown and described with reference to the structure and methods disclosed herein and as illustrated in the drawings, it is not confined to the details set forth and this invention is intended to cover any modifications and changes as may come within the scope and spirit of the following claims.

What is claimed is:

1. An end cap for a chemical processing cuvette with integrated optical analytical capability, comprising:
    a sealing portion of said end cap for sealing said cuvette, said sealing portion configured to provide a liquid-tight seal to said cuvette; and
    an optical probe portion of said end cap, said optical probe portion configured to provide optical confinement of light therein, said optical probe portion configured to avoid physical immersion in a fluid contained within said cuvette.

2. The end cap for a chemical processing cuvette with integrated optical analytical capability of claim 1, wherein said optical probe portion comprises a lens at said distal end thereof.

3. The end cap for a chemical processing cuvette with integrated optical analytical capability of claim 1, wherein said optical probe portion comprises a structure configured to provide total internal reflection.

4. The end cap for a chemical processing cuvette with integrated optical analytical capability of claim 1, further comprising a shoulder section configured to center the probe section within said cuvette.

5. The end cap for a chemical processing cuvette with integrated optical analytical capability of claim 1, further comprising a lens disposed on an end of said end cap external to said cuvette.

6. A fast optical system for free space coupling of optical radiation emanating from a chemical processing cuvette, comprising:
    an illumination source configured to provide pump radiation at a first wavelength;
    a detector configured to receive a beam of electromagnetic radiation at a wavelength different from said pump radiation at said first wavelength, and configured to provide an output signal representing at least one property of said received electromagnetic radiation;

a computer-based controller for controlling said illumination source and said detector, and additionally configured to analyze said output signal provided by said detector and to provide a result based on said output signal;

a chemical processing cuvette configured to contain a liquid of interest;

an end cap for a chemical processing cuvette with integrated optical analytical capability according to claim 1;

a beam splitter and filter configured to pass pump radiation at said first wavelength into said chemical processing cuvette by way of said end cap, and configured to pass electromagnetic radiation at a wavelength different from said pump radiation at said first wavelength from said cuvette by way of end cap to said detector; and one or more lenses separated from said end cap, said one or more lenses configured to shape said beam of electromagnetic radiation to illuminates said detector.

7. The fast optical system for free space coupling of optical radiation of claim 6. wherein said end cap for a chemical processing cuvette comprises a lens at said distal end thereof.

8. The fast optical system for free space coupling of optical radiation of claim 6, wherein said optical probe portion comprises a structure configured to provide total internal reflection.

9. The fast optical system for free space coupling of optical radiation of claim 6, further comprising a shoulder section configured to center the probe section within said cuvette.

10. The fast optical system for free space coupling of optical radiation of claim 6, further comprising a lens disposed on an end of said end cap external to said cuvette.

11. The fast optical system for free space coupling of optical radiation of claim 6, wherein said one or more lenses separated from said end cap comprise a concave-spherical, convex elliptical asphere.

12. The fast optical system for free space coupling of optical radiation of claim 6, wherein said beam splitter us a dichroic filter.

13. The fast optical system for free space coupling of optical radiation of claim 6, wherein said beam splitter comprises a partially transparent mirror and a filter.

14. The fast optical system for free space coupling of optical radiation of claim 6, wherein said source of pump illumination is a laser.

15. The fast optical system for free space coupling of optical radiation of claim 6, wherein said source of pump illumination is a light emitting diode.

16. The fast optical system for free space coupling of optical radiation of claim 6, wherein said source of pump illumination is a source of illumination configured to provide a broad range of wavelengths and an associated monochromator.

17. The end cap for a chemical processing cuvette with integrated optical analytical capability of claim 1, comprising:

a sealing portion of said end cap for sealing said cuvette, said sealing portion configured to provide a liquid-tight seal to said cuvette; and an optical probe portion of said end cap, said optical probe portion configured to provide optical confinement of light therein, said optical probe portion configured to avoid physical immersion in a fluid contained within said cuvette;

in combination with:

an illumination source configured to provide pump radiation at a first wavelength;

a detector configured to receive a beam of electromagnetic radiation at a wavelength different from said pump radiation at said first wavelength, and configured to provide an output signal representing at least one property of said received electromagnetic radiation;

a computer-based controller for controlling said illumination source and said detector, and additionally configured to analyze said output signal provided by said detector and to provide a result based on said output signal;

a chemical processing cuvette configured to contain a liquid of interest;

a beam splitter and filter configured to pass pump radiation at said first wavelength into said chemical processing cuvette by way of said end cap, and configured to pass electromagnetic radiation at a wavelength different from said pump radiation at said first wavelength from said cuvette by way of end cap to said detector; and one or more lenses separated from said end cap, said one or more lenses configured to shape said beam of electromagnetic radiation to illuminates said detector.

* * * * *